US012697043B2

(12) United States Patent
Stine et al.

(10) Patent No.: US 12,697,043 B2
(45) Date of Patent: Aug. 4, 2026

(54) BIOIMPEDANCE SENSOR-INTEGRATED CAPSULE FOR MONITORING

(71) Applicants: University of Maryland, College Park, College Park, MD (US); JOHNS HOPKINS UNIVERSITY, Baltimore, MD (US)

(72) Inventors: Justin Stine, La Plata, MD (US); Luke A. Beardslee, Atlanta, GA (US); Reza Ghodssi, Potomac, MD (US); Brian Holt, Huntingtown, MD (US); Vivian Borbash, College Park, MD (US); Hossein Abianeh, Gaithersburg, MD (US); Michael Straker, Severn, MD (US); Joshua Levy, Lanham, MD (US); Pankaj J. Pasricha, Baltimore, MD (US)

(73) Assignee: University of Maryland, College Park, College Park, MD (US)

( * ) Notice: Subject to any disclaimer, the term of this patent is extended or adjusted under 35 U.S.C. 154(b) by 332 days.

(21) Appl. No.: 18/329,533

(22) Filed: Jun. 5, 2023

(65) Prior Publication Data

US 2023/0404428 A1 Dec. 21, 2023

Related U.S. Application Data

(60) Provisional application No. 63/365,845, filed on Jun. 3, 2022.

(51) Int. Cl.
| | |
|---|---|
| *A61B 5/07* | (2006.01) |
| *A61B 1/00* | (2006.01) |
| *A61B 5/00* | (2006.01) |

(52) U.S. Cl.
CPC .......... *A61B 5/073* (2013.01); *A61B 1/00016* (2013.01); *A61B 5/0031* (2013.01); *A61B 2560/0209* (2013.01)

(58) Field of Classification Search
CPC ........ A61B 5/073; A61B 5/0538; A61B 1/041
See application file for complete search history.

(56) References Cited

U.S. PATENT DOCUMENTS

| | | | |
|---|---|---|---|
| 8,952,192 B2 | 2/2015 | Sintim et al. | |
| 9,629,586 B2 | 4/2017 | Ghaffari et al. | |
| (Continued) | | | |

FOREIGN PATENT DOCUMENTS

| | | | | |
|---|---|---|---|---|
| CN | 104970757 A | 10/2015 | | |
| CN | 115299886 A | 11/2022 | | |
| WO | WO-2020081904 A2 * | 4/2020 | ............ | C12M 41/48 |

OTHER PUBLICATIONS

Wang et al. "Capsule-Based Measurements of Gastrointestinal Impedance." (2015). 14 pages.
(Continued)

*Primary Examiner* — Tammie K Marlen
(74) *Attorney, Agent, or Firm* — Quarles & Brady LLP

(57) ABSTRACT

The present disclosure describes various aspects of various devices, and methods of making and using the devices, for measuring bioimpedance of tissues within a patient's body, such as GI tract tissue. The devices entail using various implementations of capsules or other housings that allow for ingestion or other insertion into a body of the device, equipped with microfabricated sensors and embedded circuitry enabling wireless communication. Among other benefits, this approach addresses a gap in conventional GI tract monitoring devices and methods to non-invasively access the small intestine and directly measure the inflammatory state of intestinal tissue, including ischemia, edema, and mucosal abnormalities. The device integrates 1) bioimpedance measurements resulting from transmural contact of tetrapolar electrodes against intestinal tissue; 2) a packaging scheme for molding the electronics in a biocompatible polymer/resin and conformally wrapping the sensor on the
(Continued)

surface of the capsule; and 3) a circuit configuration for signal acquisition and real-time wireless transmission to an external receiver.

8 Claims, 9 Drawing Sheets
(8 of 9 Drawing Sheet(s) Filed in Color)

(56)                    References Cited

U.S. PATENT DOCUMENTS

| | | | |
|---|---|---|---|
| 10,219,748 B2 | 3/2019 | Terry et al. | |
| 10,842,438 B2 | 11/2020 | Jiang et al. | |
| 11,134,884 B2 | 10/2021 | Gregersen et al. | |
| 11,547,347 B2 | 1/2023 | Dagdeviren et al. | |
| 2003/0195400 A1* | 10/2003 | Glukhovsky | A61B 5/0538 |
| | | | 600/302 |
| 2019/0175110 A1 | 6/2019 | Gregersen et al. | |
| 2021/0213264 A1 | 7/2021 | Liu et al. | |
| 2022/0041973 A1 | 2/2022 | Stine et al. | |

OTHER PUBLICATIONS

Zhang et al. "Nfcapsule: An ingestible sensor pill for eosinophilic esophagitis detection based on near-field coupling." Proceedings of the 20th ACM Conference on Embedded Networked Sensor Systems. 2022. 16 pages.

* cited by examiner

Start

902 Obtain information for tissue of interest

904 Determine bioimpedance interrogation frequency

906 Set electrode size characteristic

908 Determine electrode placement

910 Prepare housing

912 Assemble components on and within the housing

BIOIMPEDANCE SENSOR-INTEGRATED CAPSULE FOR MONITORING

CROSS REFERENCE TO RELATED APPLICATIONS

The present application is based on, claims priority to, and incorporates herein by reference in its entirety for all purposes, U.S. Provisional Patent Application Ser. No. 63/365,845, filed Jun. 3, 2022.

STATEMENT OF GOVERNMENT SUPPORT

This invention was made with government support under ECCS1939236 awarded by the National Science Foundation. The government has certain rights in the invention.

TECHNICAL FIELD

The various methods, systems, devices, and processes described herein relate generally to the field of bioimpedance sensing within a patient's body. In specific embodiments, the disclosure herein describes bioimpedance sensing throughout a patient's GI tract via ingestible device.

BACKGROUND

Gastrointestinal disorders, such as Crohn's disease and ulcerative colitis (UC), chronically affect approximately 20 million Americans. These disorders are intimately linked with imbalances of the gut microbiome; however, the underlying etiology is unclear. Thus, diagnosis predominantly relies on observation of symptoms, instead of explicit biomarkers. A persistent commonality between distinct types of GI disorders is the occurrence of tissue inflammation and deterioration of tissue integrity, though the severity, location, and characteristics of the inflammation differs. Tissue inflammation results in increased tissue fluid content, and the deterioration of tissue integrity yields lower connectivity between tissue cells. These changes in tissue properties impact the conductivity at the surface of and throughout the layers of the epithelial tissue, which can be characterized through quantitative electrochemical analysis. Of the available physiological electrochemical sensing approaches used for diagnosis, researchers have predominantly relied on transepithelial electrical resistance, or TEER, measurements to evaluate the permeability of epithelial tissues and cell culture. However, TEER requires electrodes to be placed on both sides of the tissue, which is not always possible in vivo due to the damaging effects of tissue penetration by the sensing electrodes. Therefore, while TEER possesses many benefits for better understanding tissue integrity, its application is limited to in vitro or ex vivo contents and is not well-suited for evaluating the state of tissue health in the GI tract where the location of inflamed tissue is unknown.

SUMMARY

The present disclosure devices and methods that overcome the aforementioned drawbacks by measuring epithelial impedance of small bowel tissue using an ingestible capsule embodiment equipped with microfabricated sensors and embedded circuitry enabling wireless communication. This approach addresses a gap in gastrointestinal diagnosis and treatment methods to non-invasively access the small intestine and directly measure the inflammatory state of intestinal tissue, including ischemia (decreased blood flow), edema (swelling), and mucosal abnormalities (ulcers).

In accordance with one aspect of the present disclosure, a device is described, comprising a capsule configured to be ingested by a patient and traverse the patient's gastro-intestinal tract, the capsule comprising a processing circuit, a power source connected to provide power to the processor, and a bioimpedance sensor comprising electrodes arranged on an outer surface of the capsule. The bioimpedance sensor is in electrical communication with the processing circuit through an opening in the capsule to provide a bioimpedance signal to the processing circuit measured by the electrodes. The device further includes a transmitter connected to wirelessly communicate data from the processing circuit outside the patient's body while the capsule is traversing the patient's gastro-intestinal tract.

In accordance with another aspect of the present disclosure, a method of making an ingestible sensing capsule is described, the method comprising the steps of fabricating a bioimpedance sensor including a plurality of electrodes, wherein the sensor is configured to contact an inner surface of a subject's gastro-intestinal (GI) tract. Further, the method includes fabricating a housing configured to traverse the subject's GI tract, wherein the housing having a cross-sectional dimension sized so as to reduce effects of sensor contact pressure sensor against the GI tract on output of the sensor, relative to a geometry of the electrodes. The method further includes integrating the sensor, a printed circuit board (PCB), and one or more batteries with the housing.

These aspects are nonlimiting. Other aspects and features of the systems and methods described herein will be provided below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing features of embodiments will be more readily understood by reference to the following detailed description, taken with reference to the accompanying drawings, in which:

FIG. 4(i-iii) show views of lift-off process results in patterned Cr/Au traces on Kapton film. FIG. 4(iv-vi) show views of assembled electronics inserted into a 3D-printed shell exposing a port for the impedance sensor.

FIG. 7 is a plot of the layered tissue model of bioimpedance sensitivity distribution with target depth plotted against inner electrode spacing, D, according to aspects of the present disclosure.

DETAILED DESCRIPTION

Figure 1:
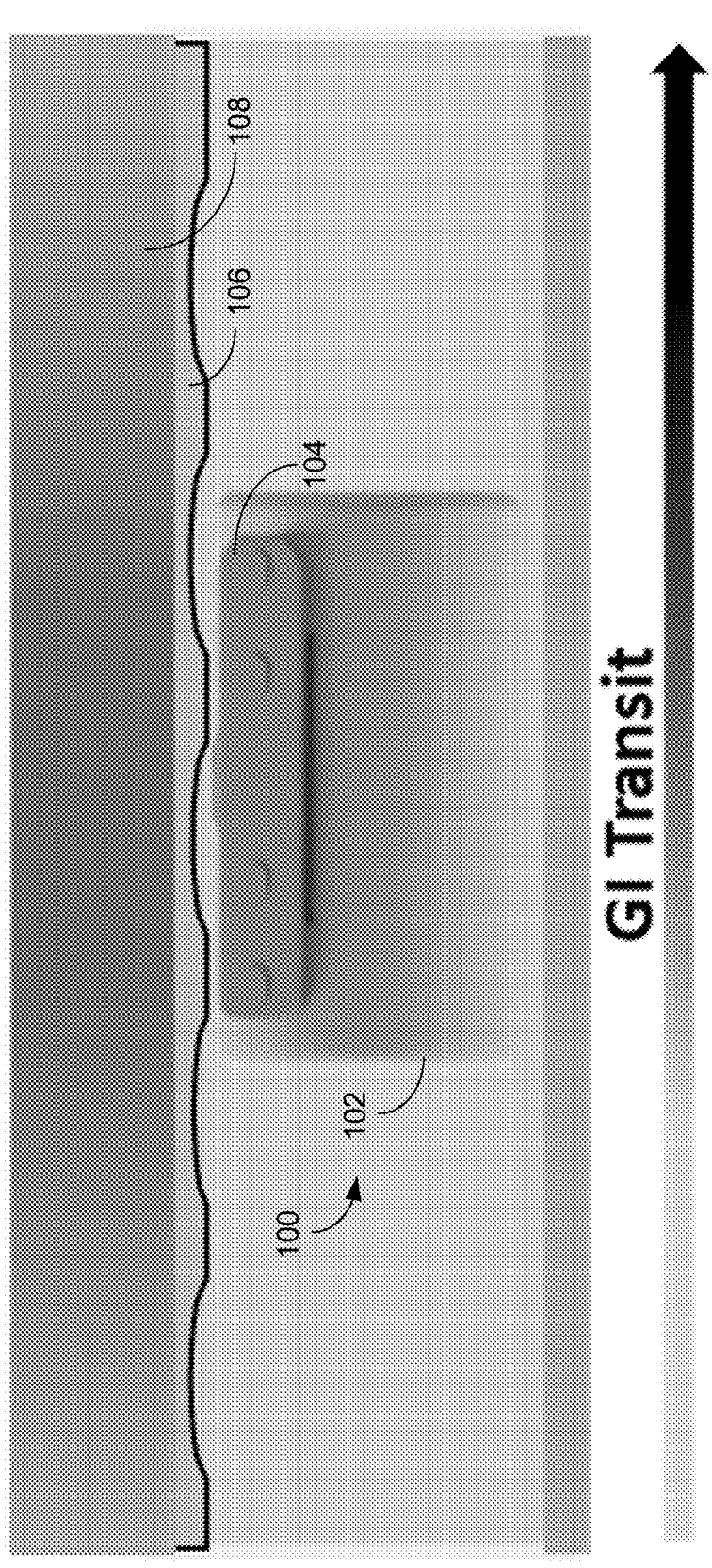
FIG. 1 is a schematic overview of an impedance sensor equipped ingestible capsule, according to aspects of the present disclosure.

As used in this specification and the claims, the singular forms "a," "an," and "the" include plural forms unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or "B" or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

Bioimpedance sensing is a promising electrochemical technique that measures the properties of tissue as a function of frequency. Electrodes are easily scalable and can be placed transmurally along the GI tract wall to measure mucosal integrity and impedance, distinguishing between inflamed and non-inflamed tissue. This technique has been employed for a wide variety of medical applications, including wearable devices. For easily accessible regions of the GI tract, such as the esophagus, researchers have utilized existing, externally-manipulated, examination technologies to detect and monitor tissue inflammation. For example, devices such as endoscopic probes, equipped with physiological sensors and/or embedded cameras have been widely commercialized, though these devices have limited or no applicability to target tissue integrity locally, especially for the small bowel.

Bioimpedance sensors have been used topically to gather physiological information through the skin and monitor the health of surface conditions such as wound healing, leg swelling, and bruising or redness. There exist commercially available wearable and surface level impedance measurement devices for evaluation of body composition (fat, muscle, and hydration). These systems utilize differences in current carrying capacity of different tissue types to ascertain information about the relative composition of the body. Because BIA also gives information about cellular level architecture, this method can be used to non-invasively evaluate the progression of wound healing. The inventors have determined, however, that bioimpedance sensing techniques can be applied to gather information useful to understanding cellular architecture at a variety of points throughout in the GI tract, thus advancing from and overcoming deficiencies of the prior art.

Sensors have also been integrated with endoscopes for measuring mucosal impedance. Although these endoscopes are capable of investigating GI barrier integrity, they carry with them the costs and risks associated with sedation, along with limited access to the intestines. The inventors have therefore developed embodiments and methods that utilize ingestible capsules to overcome this limitation as they are capable of traversing the entire gastrointestinal tract in a less invasive manner.

Referring now to FIG. 1, a diagram is shown to generally illustrate some of the bioimpedance principles that are leveraged by the various embodiments of devices and methods presented herein. For example, some embodiments leverage a systems integration approach to provide a device 100 having a miniaturized housing 102 (such as a capsule or other housing capable of being ingested and/or otherwise placed into a patient's body, such as the GI tract) that can be equipped with an external bioimpedance sensor 104. The sensor 104 can assess tissues 106 using bioimpedance interrogation to determine various states, such as for a variety of inflammatory conditions, including ischemia, edema, and chronic swelling from GI disorders. In other words, as the device 100 traverses a patient's GI tract, the sensors 104 make contact with tissues of interest 106, and apply an interrogation signal to the tissue, thus generating an output that is recorded and can later be used to assess various conditions or state of the tissues 108. As will be explained below, the various ways in which these sensors are presented to the tissues of interest provide for improved sensitivity, selectivity, and accuracy of bioimpedance measurements throughout an entire GI tract (or any portion thereof desired by a clinician). And, given the onboard processing available, and ease of design selection for the dimensions and geometry of the housing and sensors, various embodiments described herein can be tailored in design to maximize and/or improve their ability to generate bioimpedance sensing measurements for various tissue types, tissue depths, and other factors of interest.

In one aspect, the present disclosure describes a device and method of making the device that will serve as an investigative tool for measuring epithelial impedance of small bowel tissue (FIG. 1). In a non-limiting example, a microfabricated bioimpedance sensor will be attached to an ingestible capsule and used to indicate and characterize a range of GI inflammatory conditions. One example is monitoring ischemia, which is described as decreased blood flow to the intestines. This condition results in lowered metabolic energy of affected tissue due to the lack of oxygen flow, allowing extracellular fluid to penetrate into the cell, thus causing an increase in conductivity.

In a non-limiting example, the bioimpedance ingestible capsule includes tetrapolar Kapton-based electrodes that utilize a geometry designed to achieve a targeted penetration depth of the excitation signal tuned for small intestinal tissue to monitor layers of the tissue that contribute to a variety of inflammatory conditions, including ischemia, edema, and chronic swelling from GI disorders.

In accordance with one aspect of the present disclosure, a device comprising a capsule, a power source, a bioimpedance sensor, and a transmitter is described. The capsule is configured to be ingested by a patient and traverse the patient's gastrointestinal tract (GI). In a non-limiting example, the capsule is cylindrical with a diameter between 4-20 mm and length between 1-35 mm. Capsule diameter is linked to contact pressure. The maximum diameter of the capsule is limited by the esophagus, which is the most narrow segment of the GI tract. Although ingestible capsules that are smaller in diameter are easier to pass, it is suspected that faulty contact with tissues could be a potential source of noise. Larger radius electrodes are more likely to make contact with tissues and may be necessary for smaller capsule designs. Although they target the mucosal layer, smaller radius electrodes may be better suited for larger capsules, since less surface area exists to interface with the tissue. Tissue contact is pivotal for continuous GI monitoring using bioimpedance. In a non-limiting example, the capsule is a soft, biocompatible material such as, but not limited to, polymers or epoxy resins. For example, a biocompatible polymer may include polylactic acid (PLA) or a polymeric compound such as polydimethylsiloxane (PDMS). According to one example, PDMS may be mixed in a 10:1 base to hardener ratio to achieve the appropriate material properties to insulate the internal capsule components from a liquid environment.

Figures 2A, 2B:
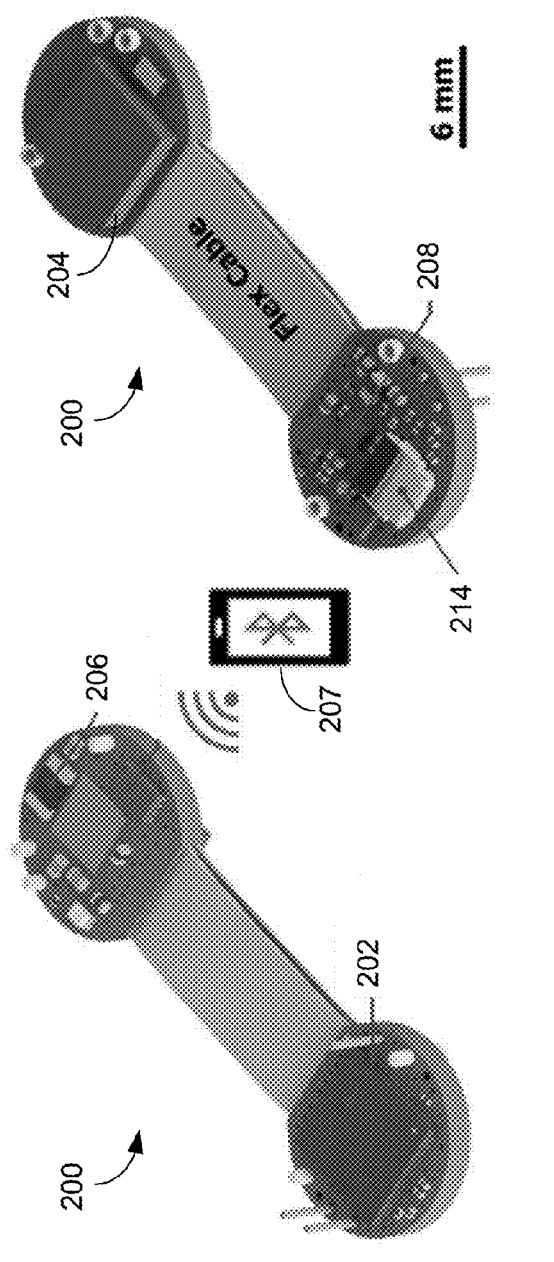
FIG. 2A is a schematic overview of capsule electronics a flex-rigid PCB according to aspects of certain example embodiments the present disclosure.
FIG. 2B is a circuit diagram of a processing circuit used to operate the impedance sensor according to aspects of the present disclosure.

Referring to FIGS. 2A-2B, a non-limiting example of a processing circuit configured to be positioned within the capsule is shown. The processing circuit 200 includes a potentiostat integrated analog-front end circuit 202 and a Bluetooth® Low Energy microcontroller 204. The Bluetooth® Low Energy microcontroller 204 is configured to interface the sensor with an external receiving device 207 such as a computer, tablet, mobile phone, or other user device. As shown in FIGS. 2A-2B the processing circuit 200 may be arranged on a printed circuit board (PCB). In a non-limiting example, the PCB layout is designed using EAGLE (Autodesk, San Rafael, CA) to create the electronics board: a flex-rigid PCB, containing analog-front end (AFE) circuitry 202 and Bluetooth Low Energy (BLE) microcontroller (MCU-BLE) 204. Specifically, the flex-rigid PCB 200 incorporates several components: (1) an AFE potentiostat IC (AD5941, Analog Devices) 202 for generating sensor excitation signals, as well as to amplify the output current of the sensor and digitize the signal using an onboard analog-to-digital converter, (2) an MCU-BLE 204 (BGM13S, Silicon Labs) paired with an external 2.45 GHz antenna 206 (WLA.01, Taoglas) for wireless data acquisition (signal power: 0-+18 dBm) and energy management, and (3) a 3.3 V voltage regulator 208 (TPS610981, Texas Instruments), paired with a 3.0 V lithium manganese coin cell battery 210 (2L76, Energizer) and a magnetic reed switch 212 (HSR-502RT, Hermetic Switch) to power the electronics.

However, it is to be understood that the specific processing circuitry components to be used in various embodiments need not be limited to those described herein. In particular, a variety of processors and microcontrollers may be utilized, so long as they meet certain design criteria: they should have a form factor that fits within a given capsule/housing (the size of which can vary, as described below), should have a power consumption that can be addressed by the size and capacity of batter that can be included in the housing, and should be able to have sufficient processing speed to acquire and transmit data from the bioimpedance sensor. In yet further embodiments, the microcontroller may have a memory associated with it that permits more complex routines to be run on the processing unit of the microcontroller. For example, the microcontroller may selectively change or sweep frequencies of the interrogation current (whether autonomously or via pre-set programming), may respond to control instructions from an external device, and may react to the types of signals it determines. For example, a pH-sensitive coating may cover a separate contact on the exterior of the capsule, configured to dissolve at a select point in the GI tract. When the coating has dissolved and the contact is exposed, the processor may detect a signal and begin or cease, or increase/decrease sampling rate of, bioimpedance detection. In other embodiments, the microcontroller may be programmed to assess bioimpedance values and react accordingly: for example, increasing sampling rate when bioimpedance values within a target range are detected, and decreasing sampling rate/increasing delay between samplings when bioimpedance values have been exhibiting normal ranges for a given time period. Similarly, if a given bioimpedance measurement is detected, the processor may cause the signal generator/potentiostat to increase or decrease frequency, to obtain measurements that have more or less contribution of various parts of the tissue of interest, as described further below.

Similarly, rather than a mere antenna to act as a transmitter, a transceiver and/or separate receiver may be utilized. These embodiments would allow for bi-directional communication between an external control device and the capsule device.

In a non-limiting example, the AFE potentiostat IC 202 may generate an interrogation frequency ranging from 100 Hz to 1 MHz. In a preferred embodiment, the interrogation frequency ranges from 1-10 kHz. This 1-10 kHz frequency range displays minimal dependency on contact pressure and is less susceptible to stray capacitances. Further, at this frequency range, the measured impedance contribution is derived from both extracellular and intracellular spaces.

In a non-limiting example, the flex-rigid PCB may be commercially fabricated on a double-sided 6-layer FR-4 ceramic substrate with embedded polyimide flex regions (15 mm in length) connecting the traces between two rigid boards (Sierra Circuits, Sunnyvale, CA), thus allowing the PCB to bend (FIG. 2A). In one example, when bending the flex regions (bend radius: 1.2 mm) no significant changes to signal noise were observed. All traces between the MCU 204 and AFE 202 (across the flex region) connect digital inputs and outputs, as well as VDD and GND, and do not influence recorded impedance measurement. Analog signals are processed directly between the bioimpedance sensor and AFE 202. In a non-limiting example, the flexible sensor is attached to the AFE 202 using a 4-pin 0.5 mm pitch flat flex connector (FFC) interface 214. The capsule features an opening around the impedance sensor port. Once inserted, the sensor is contoured around the exterior of the shell and sealed using epoxy.

In a non-limiting example, the power supply connected to provide power to the processor is one or more batteries. For example, a coin cell battery (160 mAh) may be connected to the flex-rigid PCB using 30-gauge threaded wire fixed with copper and Kapton tapes, while the magnetic reed switch was soldered between the (+) battery terminal and the voltage regulator.

Figure 3:
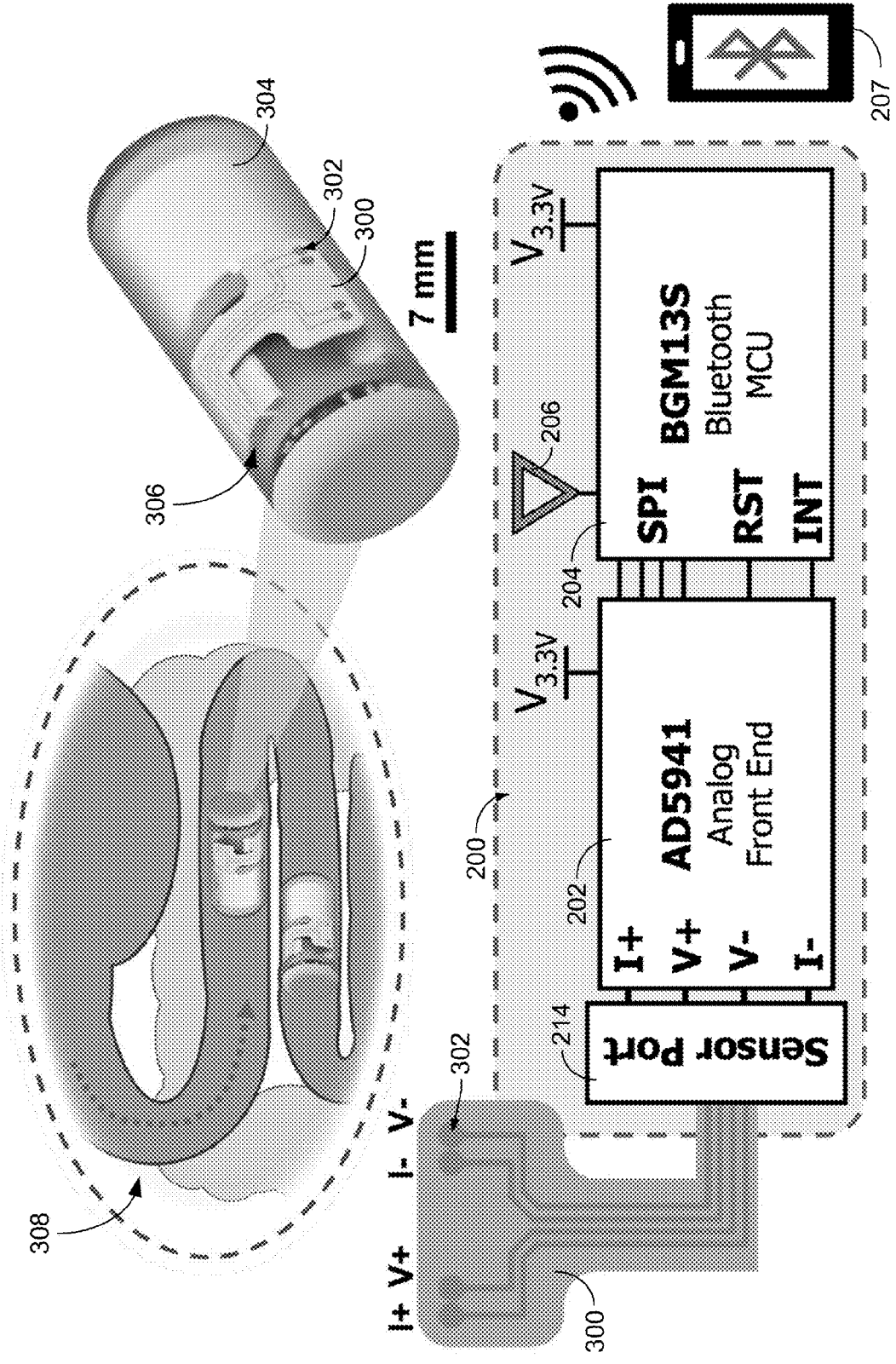
FIG. 3 is a schematic overview depicting an ingestible capsule monitoring bioimpedance in the small intestine and an associated circuit diagram of the device, according to various aspects of example embodiments the present disclosure.

Referring to FIG. 3, a depiction 308 of a bioimpedance sensor device traversing a GI-tract is shown. In contrast to previous techniques for attempting to measure bioimpedance within the GI-tract, as can be seen the device does not require an external component in order to measure bioimpedance. Rather, bioimpedance is measured entirely from within the GI-tract. Additionally, because the device was ingested orally, it is capable of measuring bioimpedance throughout the entire GI-tract. In other words, the device is sized so as to be swallowable by a patient and pass through the narrowest part of the GI-tract, which for human patients is often the esophagus. traverses the entire GI-tract, whereas endoscopes and other such equipment are not capable of passing into lower GI areas such as the intestines. In a non-limiting example, the bioimpedance sensor 300 comprises electrodes 302 arranged on an outer surface of the capsule 304 and is in electrical communication with the processing circuit through an opening 306 in the capsule 304 to provide a bioimpedance signal to the processing circuit 200 measured by the electrodes 302.

Figure 4:
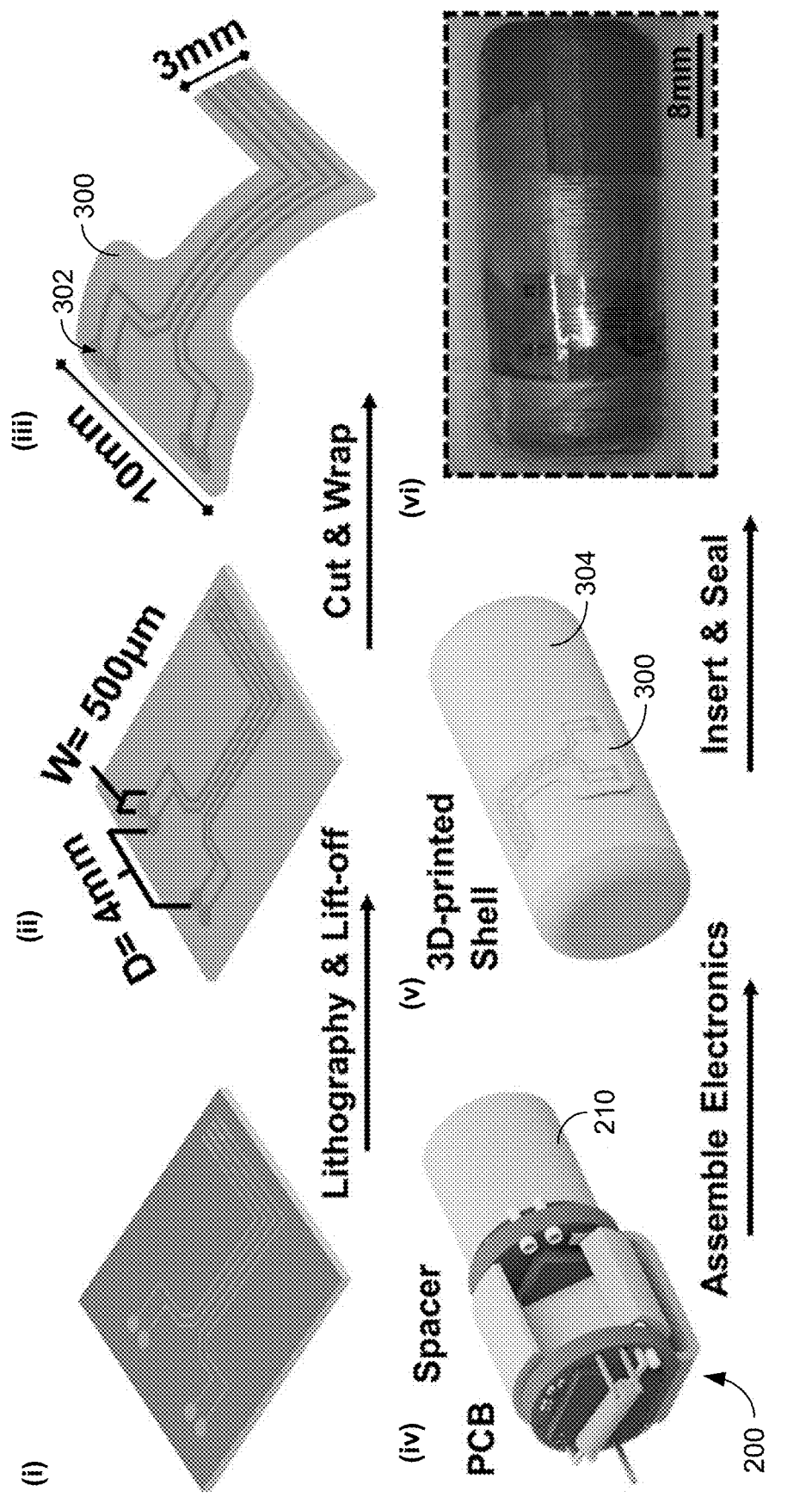
FIG. 4 is a summary of an ingestible bioimpedance sensing device fabrication process and capsule prototype assembly according to various possible configurations of embodiments of the present disclosure.
Figure 5:
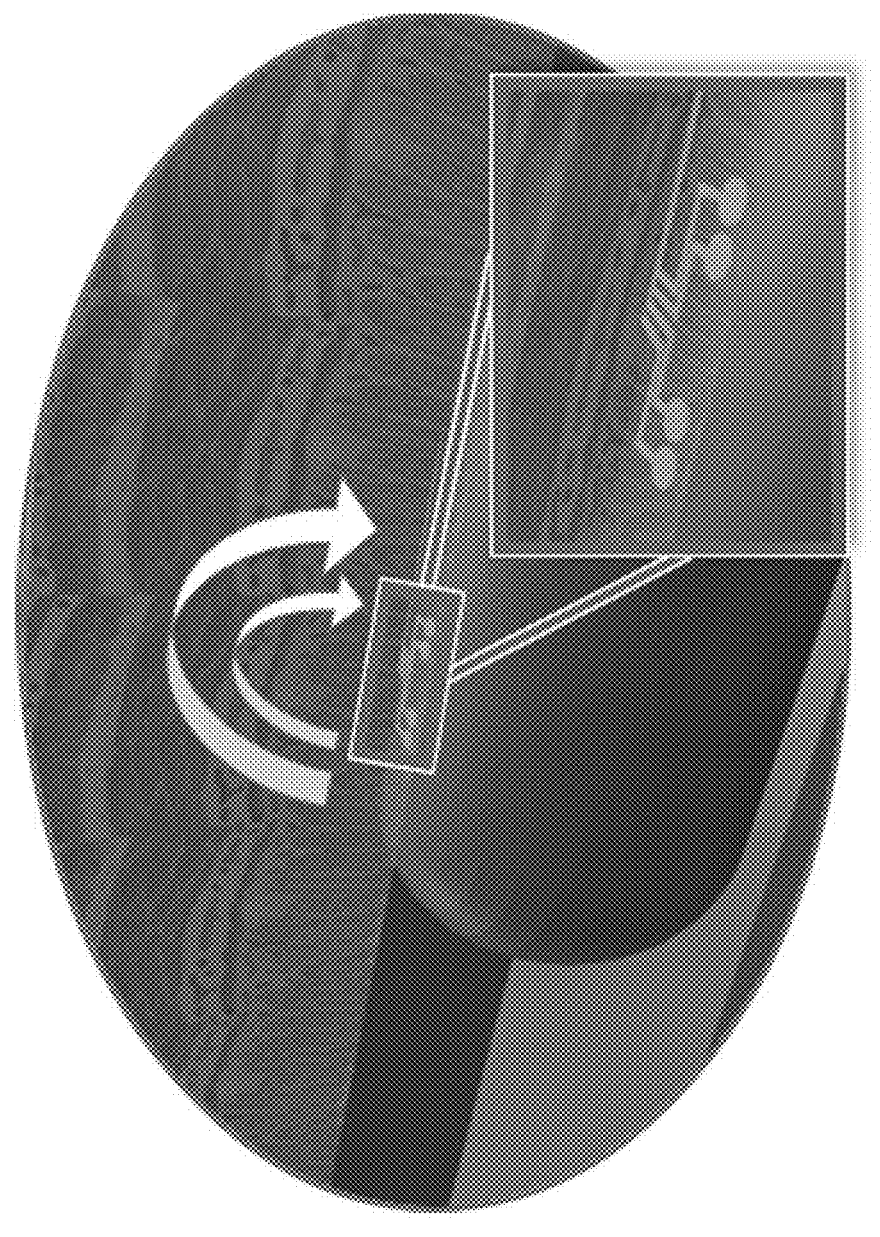
FIG. 5 is a diagram showing a capsule-mounted sensor injecting current through epithelial tissue of the GI tract.

FIG. 4 illustrates the steps ((i)-(vi)) of assembling an ingestible bioimpedance sensing device, according to aspects of the present disclosure. As shown in steps (i)-(iii), the bioimpedance sensor may be fabricated using traditional microfabrication techniques. The electrodes may be made of gold (Au) or any suitable electrode material. Further, the electrodes may be circular or disk-shaped ranging in diameter from 0.001-10 mm. In a non-limiting example, the bioimpedance sensor consists of four linearly arranged 500 μm circular Au electrodes with spacing parameters determined via simulation results. In this example, the four electrodes are arranged in a Schlumberger configuration, wherein the outer electrodes and inner electrodes are for current-injection and voltage sensing, respectively (FIG. 5). In a non-limiting example, to eliminate the contribution of contact polarization impedance, four electrodes are used in the fabricated bioimpedance sensor. In a non-limiting example, the distance between the two inner electrodes ranges is at least 0.001 mm. The upper limit of the distance between the two inner electrodes is defined by the design constraints of the ingestible capsule. In a preferred embodiment, the distance between the two inner electrodes is 0.001-10 mm. In a non-limiting example to meet the design constraints of the ingestible capsule, the distance between the outer electrodes is limited to 15 mm and the spacing between inner and outer electrodes was fixed to 100 μm. These dimensions help to minimize the negative sensitivity regions, while providing flexibility in the creation of the sensor mask and subsequent fabrication of the sensor.

In a non-limiting example in steps (i)-(iii), the tetrapolar electrode configuration was fabricated using a lift-off process on a 25.4 μm thick flexible polyimide substrate with Cr/Au (20 nm/100 nm). The polyimide substrate was carefully affixed to a silicon carrier wafer using Kapton tape, and air pockets were removed using an ink roller. A positive photoresist, Shipley S1813, was uniformly applied (spun) onto the substrate and the desired sensor pattern was achieved after exposure of a 365 nm UV light through a prepared photomask. Prior to metal deposition the electrodes were treated in an O2 asher (1 min at 150 W) to further clean the surface of the substrate. Electron-beam evaporation was used to deposit a thin film of chromium and gold (Cr/Au) in thicknesses of 20 nm and 100 nm, respectively. The Cr layer served to improve adhesion of gold to the Kapton film. The final pattern was resolved after sonicating the wafers in acetone for 15 minutes. To prevent shorting between the electrodes and traces, the sensors were solvent cleaned and dried with nitrogen, then coated with 2 μm of Parylene-C. Shipley S1813 was once again utilized to pattern a dry etch mask following the previously described photolithography steps, and reactive ion etching (ME) was used to dry etch the Parylene-C. The final pattern consisted of exposed electrodes and contact pads; however, the traces were insulated.

In a non-limiting example, the device may be constructed using a 3D-printed mold structure to encapsulate the electronics inside the capsule (step (iv)-(v)). Using a biocompatible material such as epoxy or PDMS mixed in a 10:1 base to hardener ratio to achieve the appropriate material properties to insulate the electronic components from a liquid environment, the structure can be molded multiple times with this method allowing interchanging of microfabricated impedance sensors and rapid characterization of sensor performance. In a non-limiting example, the device dimensions are between 13 mm in diameter and 35 mm in length, following the standard for cylindrical capsules. In this example, the rectangular mold consisted of a cylindrical inner cavity to mount the processing circuit and battery power supply and a tapered opening on the top to allow PDMS to be poured into the cavity. To prevent PDMS from leaking during the curing process an O-ring was placed around the cylinder cavity perimeter, pressed tightly between the two mold halves, and held in place with 6 M3 thermo-inserts and screws. Additionally, to save power and keep the electronics in an OFF state while curing two neodymium magnets were placed against the 3D-printed mold, which would open the internal reed switch and temporarily disconnect the battery from the PCB. In a non-limiting example, Similar coatings of Parylene-c as a thin, conformal layer of insulation may be used on the electronics, followed by encapsulation of either PDMS or a biocompatible epoxy, such as MasterSil 151Med or EP42HT-2FG (Masterbond). Alternatively, a combination of these encapsulation approaches may be used for biocompatibility of the ingestible capsule and isolation of the internal processing circuit and power supply within the capsule.

According to another aspect of the present disclosure, a method of making an ingestible sensing capsule is described, the method comprising the steps of fabricating a bioimpedance sensor including a plurality of electrodes, wherein the sensor is configured to contact an inner surface of a subject's gastro-intestinal (GI) tract. Further, the method includes fabricating a housing configured to traverse the subject's GI tract, wherein the housing having a cross-sectional dimension sized so as to reduce effects of sensor contact pressure sensor against the GI tract on output of the sensor, relative to a geometry of the electrodes. The method further includes integrating the sensor, a printed circuit board (PCB), and one or more batteries with the housing.

In accordance with another aspect of the present disclosure, bioimpedance sensor design optimized for measuring the bioimpedance of the small bowel of the GI tract as shown in FIG. 5.

Specifically, by optimizing the spacing and width of the four electrodes, the bioimpedance sensor can be used to eliminate extraneous information and non-invasively monitor tissue integrity with targeted signal penetration depth in vivo.

Figure 6A:
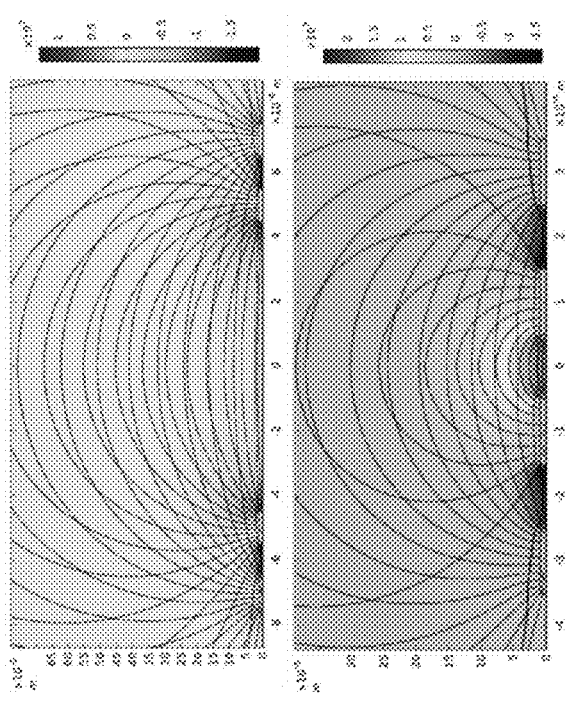
FIG. 6A shows plots of the simple sensor model for sensitivity distribution and the associated percent sensitivity contribution plotted against height.
Figure 6B:
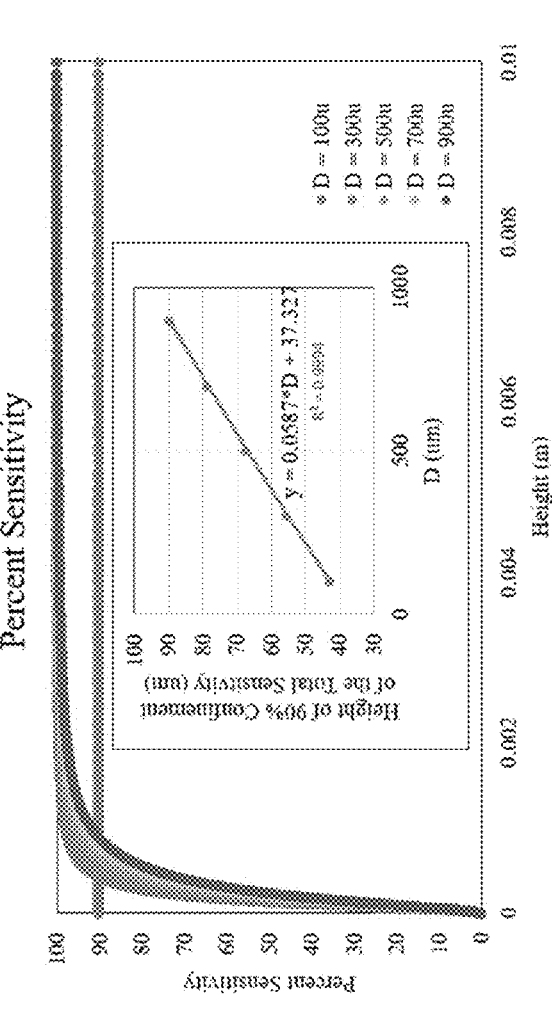
FIG. 6B is a plot of the 90th percentile sensitivity confinement height plotted against inner electrode spacing, according to aspects of the present disclosure.

In a non-limiting example, electrode design is determined using COMSOL Multiphysics through finite element modeling (FEM) to predict the impedance response at the desired tissue layers in the GI tract to inform the sensor design. For example, an FEM analysis, solver, and simulation software may be used, such as COMSOL Multiphysics. As shown in FIG. 6A, simulations may be used to optimize the spacing and width of the electrodes to minimize negative-sensitive regions and target intestinal tissue of specified thickness and electrical properties. Four terminals are used to eliminate contact impedance from the measurements. Current is injected into the outer electrodes and the potential difference is measured across the inner electrode pair. An optimal parametric value for the electrode spacing between the inner and outer electrodes defines the penetration depth of the electric field into the model epithelial tissue. This value changes depending on the specific thickness and electrical properties (conductivity and permittivity) of each mucosal layer and provides a correlation between the measured overall impedance and the impedance contribution of each layer. In a non-limiting example, a functional sensor will derive at least 90% of its measured impedance value from the defined tissue region, simulating the expected thickness and properties of the small intestine (FIG. 6B). In other non-limiting examples, a bioimpedance sensor will derive at least 80%, 85%, 95%, etc. of its measured impedance value from a tissue of interest. In the example shown in FIG. 6A, a volume with permittivity and conductivity comparable to physiological saline was used as a baseline to understand how the electrical field lines were modeled under homogeneous conditions. In a non-limiting example, the model was improved by stacking layers of various permittivity, conductivity, and thickness to model the layers of the intestine: mucus, mucosa, submucosa, muscle, and serosa. The model can be further extended to simulate expected changes in the inflamed tissue.

In a non-limiting example, the AC/DC electrical currents module may be used to assess the following metrics against the distance between the inner electrodes: (1) The height of 90th percentile sensitivity confinement (i.e., target depth); (2) The impedance contribution of targeted layers (e.g., mucosa, submucosa, mucus); (3) The difference between impedance contribution of healthy and inflamed tissue.

Figure 7:
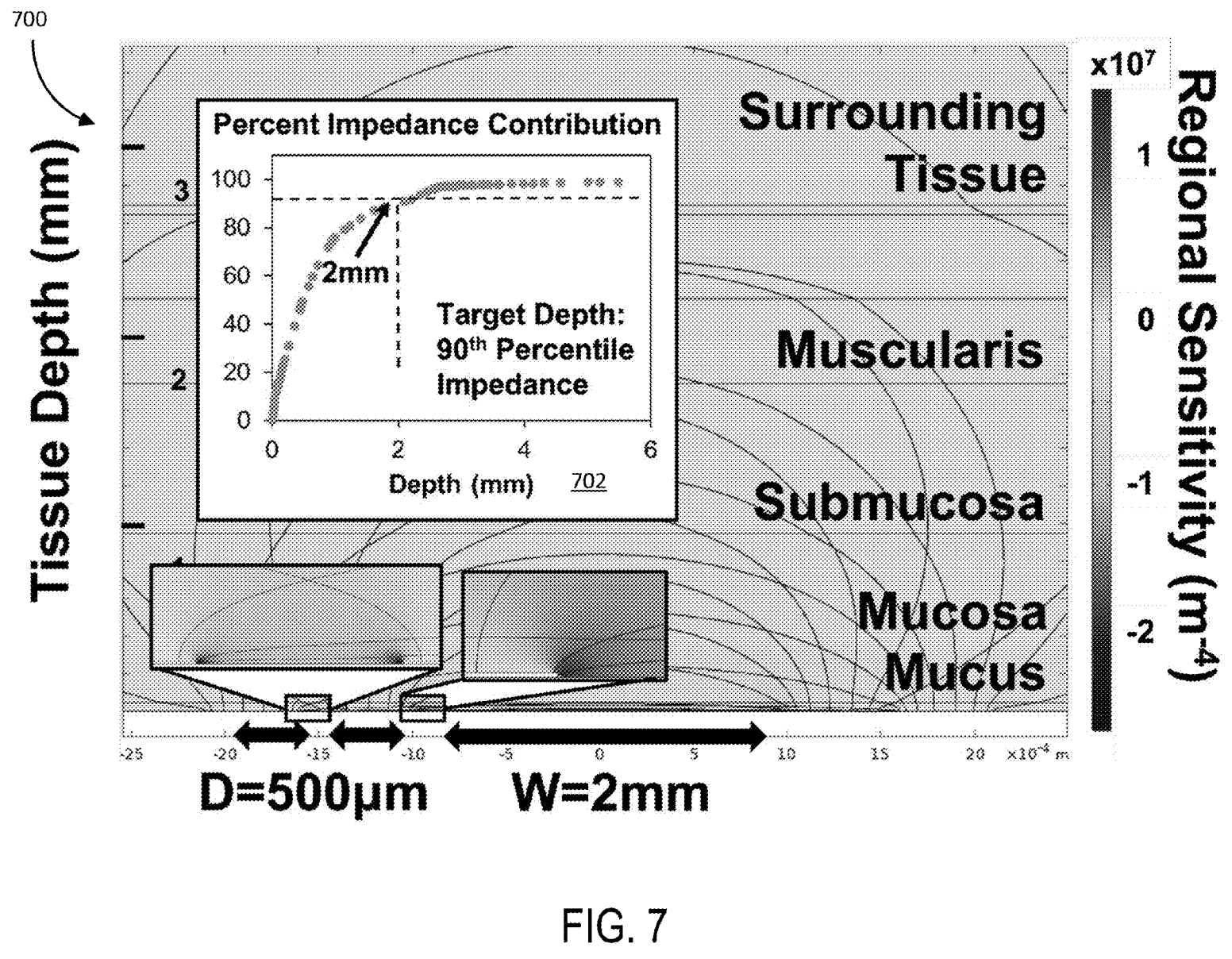

In a non-limiting example, the inner electrode spacing parameter, denoted as D in FIG. 7, was varied between 1 μm and 10 mm, while the frequency was fixed at 10 kHz and an injection current of 1 A was used. As shown in FIG. 7, for inner electrode spacing of 2.5 mm and electrode width of 500 μm, a penetration depth of 2.25 mm is achieved, corresponding to the outmost intestinal tissue layer (serosa).

An example of designing and fabricating an ingestible device for bioimpedance sensing is described in detail below to demonstrate the aforementioned device and method according to aspects of the present disclosure. The example below is not intended to be limiting.

Example Capsule Electronics

In one embodiment, the inventors fabricated a bioimpedance sensor driven by a custom flex-rigid printed circuit board (PCB) previously described. The device uses a commercially available analog front end (AFE) IC (AD5941, Analog Devices, Wilmington, MA, USA) paired with a low-power Bluetooth 5 microcontroller (BGM13S, Silicon Labs, Austin, TX, USA) and 2.45 GHz antenna (WLA.01, Taoglas, San Diego, CA, USA) for wireless transmission (up to +18 dBm) of bioimpedance data. The system is powered from a 3.0V lithium manganese dioxide battery (2L76, Energizer, St. Louis, MO, USA) supplied through a 3.3V voltage regulator (TPS610981, Texas Instruments, Dallas, TX, USA) and uses a magnetic reed switch (HSR-502RT, Hermetic Switch Inc., Chickasha, OK, USA) to disconnect the power when not in use. The sensors are inserted into a four-pin flat-flex connector (FFC) port. Electronics are housed in a capsule shell 3D-printed using polylactic acid (PLA). The shell features an opening around the impedance sensor port. Once inserted, the sensor is contoured around the exterior of the shell and sealed using epoxy. Kapton tape was used for electrical insulation of the sensor traces. Referring again to FIG. 3, an illustration of the bioimpedance capsule operating within the GI tract and sensor integration with supporting circuit diagram is shown. Kapton tape was used for electrical insulation of the sensor traces.

Tetrapolar Bioimpedance Sensor Design

In one experiment, the inventors used finite-element method (FEM) modeling to assess the influence of electrode geometrical parameters of an embodiment they fabricated, on tissue impedance contributions. Regional impedance sensitivity may be predicted using Geselowitz sensitivity theory, which maintains that the measured impedance should remain unchanged if injecting and measuring behavior of the inner and outer electrodes are exchanged. The regional sensitivity field S is defined as the normalized cross-product of these reciprocal current densities:

$$S = \frac{J_A * J_B}{I^2} \quad (1)$$

where $J_A$ and $J_B$ represent the current density fields generated when using outer and inner electrodes respectively used for current-injecting, and I is the injected current. FEM modeling of the sensitivity field was performed in COMSOL Multiphysics 5.4 (COMSOL AB, Stockholm, Sweden) using the AC/DC module. The 2D model consists of stacked rectangular tissue layers and four gold electrodes. In the model, inner and outer electrodes are spaced 100 μm apart. Regional sensitivity with respect to tissue depth and relative layer contribution was assessed for varying geometrical parameters, including electrode diameter (D) and sensor width (W).

Example Sensor Fabrication and Assembly for Experiments

To investigate how electrode geometry influences signal penetration depth and regional impedance contributions, in one experiment sensors were fabricated with varying geometry parameters. Select values for electrode diameter (D) were 500 μm, 1 mm, and 2 mm, and sensor width (W) were 2 mm, 4 mm, and 10 mm. Electrode photomasks were designed in AutoCAD (Autodesk, San Rafael, CA). The sensor shape was designed to align the electrodes along the length of the capsule and connect to an interior port oriented radially. 1 mil Kapton® Polyimide film (DuPont, Wilmington, DE, USA) was adhered to a silicon carrier wafer using double-sided tape and sensors were fabricated using a liftoff process as shown in FIG. 4. Shipley 1813 photoresist was uniformly applied using a spin-coater and samples were treated in an oxygen plasma cleaner following photolithography to improve adhesion of metal layers to the polyimide. Cr/Au (20 nm/100 nm) was deposited onto the sample via electron-beam evaporation and liftoff was performed in acetone. Electrodes were subsequently rinsed in DI water and dried with $N_2$.

Preparation of Tissue Analogues for Experiments

To understand how tissue conductivity and thickness affects the impedance magnitude response, agarose tissue phantoms were prepared using a mold containing intrusions of several depths ranging from 500 μm to 4 mm. To create the agar (Sigma Aldrich, Munich, Germany) molds, saline solutions of varying ion concentration were formed by mixing 100 mL deionized water and NaCl into a Pyrex beaker and brought to a boil using a hot plate. Next, 1.5 g of agarose powder was introduced. An additional 8.4 g of sucrose was mixed in using a stir-bar to enhance the permittivity of the resultant pucks. To simulate tissues of varying thickness, a mold was 3D-printed using PLA resin featuring circular wells. The agar solution was poured into the wells and cooled in a refrigerator for 24 h. For capsule testing ex vivo, small intestinal porcine tissue was procured (Animal Biotech Industries Inc., Doylestown, PA, USA) and cut into segments. Treated tissues were soaked in 1× phosphate buffered saline (PBS, pH 7.0) for 24 hours prior to testing.

Plotting Sensitivity

Simulation has demonstrated that deeper intestinal tissues, such as the muscularis, contribute little to the measured impedance value compared to tissue proximal to the electrodes, such as the mucosa. A negative vector (denoted with blue) appears between the inner and outer electrodes of the resultant sensitivity field, corresponding to regions which skew the measured impedance (FIG. 7). This error may be eliminated by minimizing the space between current-injecting and voltage-measuring electrodes. Thus, the embodiment of a bioimpedance sensor used in some of the inventors' experiments used a 100 μm spacing between the inner and outer electrodes, which helps to minimize negative-sensitive tissue contributions without increasing fabrication complexity. Conversely, positive-sensitive regions (red) represent tissues which disproportionately contribute to the impedance, introducing a positive gain factor. FIG. 7 depicts the COMSOL model 700 of the regional sensitivity and current field line distribution through each small intestinal tissue layer.

The inset graph 702 depicts the calculated sensitivity percentile with respect to tissue depth from the sensor for the modeled geometry using an example electrode diameter 'D' of 500 μm and sensor width 'W' of 2 mm (understanding that, in other examples, the graph would vary as D and W vary). The contribution of tissues to the measured impedance diminishes at farther tissue depths, resulting in a plateau in regional sensitivity. For the modeled geometry, the $90^{th}$ percentile impedance contribution lies at 2 mm, thus determining the sensor's "target depth." Hence, the geometry of the example electrode probes tissues within the mucus, mucosal, submucosal, and muscularis layers. Smaller electrode diameters increase the relative impedance contribution of the mucosal layer, most susceptible to damage from mucosal barrier dysfunction, which may be attributed to various physiological conditions. Hence, in one embodiment a diameter of 500 μm was chosen to maximize the bioimpedance sensor's sensitivity toward mucosal tissue. For this electrode diameter, an inner spacing of 3 mm limits fixes the target depth of the sensor to 2.25 mm, including the intestinal layers from the mucus through the circular muscularis. Increasing the sensor width W beyond this value does not substantially increase the contribution of the submucosal layer but conversely increases the contributions of surrounding tissues. Reducing the sensor width W achieves more compact sensors and may increase the relative contribution of the mucosa but limits the regional contribution of the submucosal tissue. Thus, a spacing between 2 mm and 4 mm is optimal for probing epithelial tissue layers in the small intestine.

The normalized volume integral of the sensitivity field was obtained over a region of variable distance from the sensor interface to obtain the relative impedance contribution with respect to tissue depth. Regional impedance contribution diminishes significantly beyond the depth corresponding to 90th percentile field line confinement, defined as the target depth. Simulation results indicate that electrode geometry parameters such as sensor width W (spacing between inner electrodes) and electrode diameter D affect probed tissue regions and, consequently, target depth. In this experiment, the inventors found that increasing the electrode diameter D equalized the relative impedance contribution among intestinal tissue layers. Hence, an electrode diameter of 500 μm maximized the relative contribution of the mucosal layer compared to other tested geometries for this embodiment. Additionally, the inventors determined that the target depth was related to the electrode spacing W with a proportionality constant determined by the dielectric tissue properties.

Characterization with Potentiostat

Figure 8B:
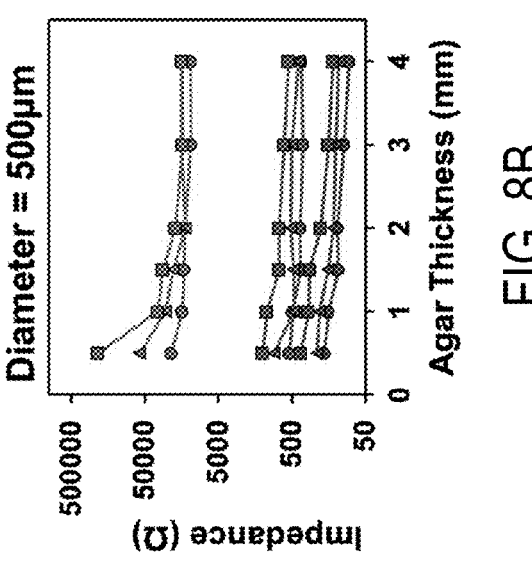
FIG. 8B is a plot of impedance recordings (at 10 kHz) of electrodes of diameter 500 μm and varying spacing (2 mm, 4 mm, and 8 mm), estimating target depth of the sensor (N=5).
Figure 8D:
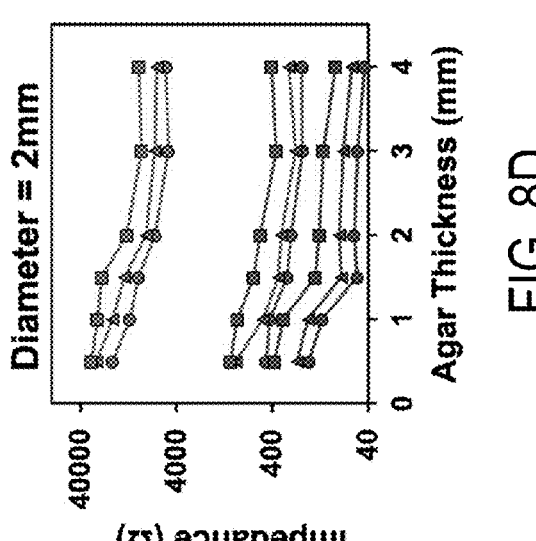
FIG. 8D is a plot of impedance recordings (at 10 kHz) of electrodes of diameter 2 mm and varying spacing (2 mm, 4 mm, and 8 mm), estimating target depth of the sensor (N=5).
Figure 8A:
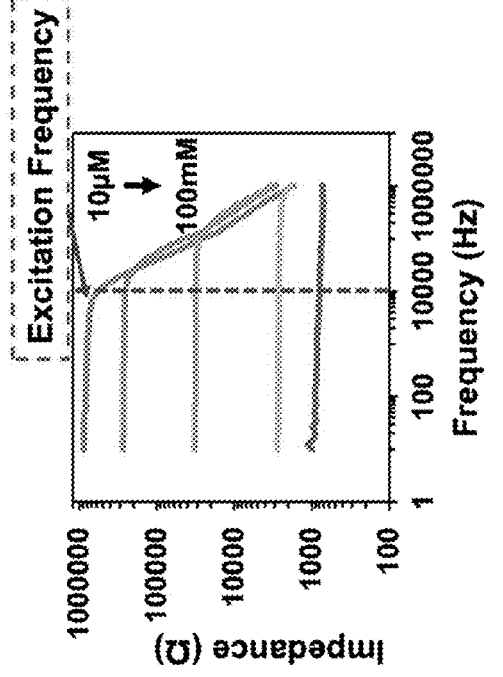
FIG. 8A is a plot of full-spectrum impedance spectroscopy at an electrode diameter, W, of 500 μm and an inner electrode spacing, D, of 4 mm.

Prior to capsule assembly, the impedance sensors of certain embodiments the inventors created were characterized using an electrochemical impedance spectroscopy (EIS) sweep in NaCl solution of varying ion concentration between 1 Hz and 1 MHz using a benchtop potentiostat (Interface 1010E, Gamry Instruments). Full-spectrum impedance analysis of the fabricated sensors in NaCl solution identified an excitation frequency of 10 kHz to minimize real impedance loss at higher frequencies and contact pressure dependence at lower frequencies. As expected, the ion concentration of the solution inversely affected the measured impedance magnitude (FIG. 8A).

Figure 8C:
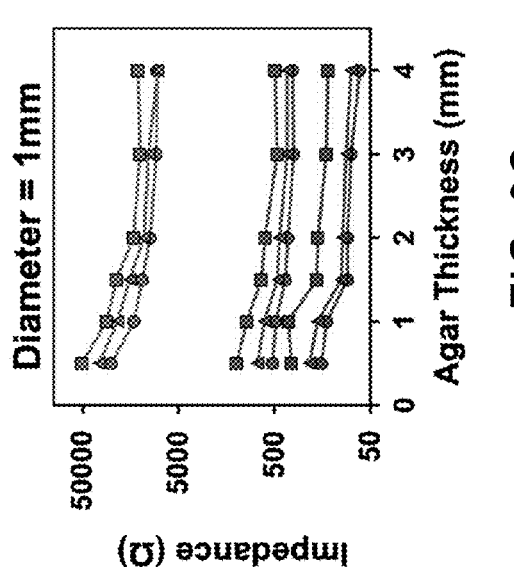
FIG. 8C is a plot of impedance recordings (at 10 kHz) of electrodes of diameter 1 mm and varying spacing (2 mm, 4 mm, and 8 mm), estimating target depth of the sensor (N=5).

To validate trends observed during FEM modeling, molded agarose tissue phantoms of varying conductivity and thickness were used to visualize the impedance response to tissue depth at the optimal interrogation frequency determined from EIS characterization in saline. Based on FEM results, as the thickness of a uniform target media increases beyond a particular point, variation in measured impedance should vanish. The target depth for each sensor configuration was determined through benchtop potentiostat characterization. The sensors exhibited a plateau in measured impedance with increasing agar thickness (FIG. 8B-8D). Using the results, a sensor geometry of D=500 μm and W=4 mm was chosen for validation ex vivo on PBS-treated porcine intestinal tissue approximately 1 mm thick.

Manufacturing Design and Fabrication Processes

Figure 9:
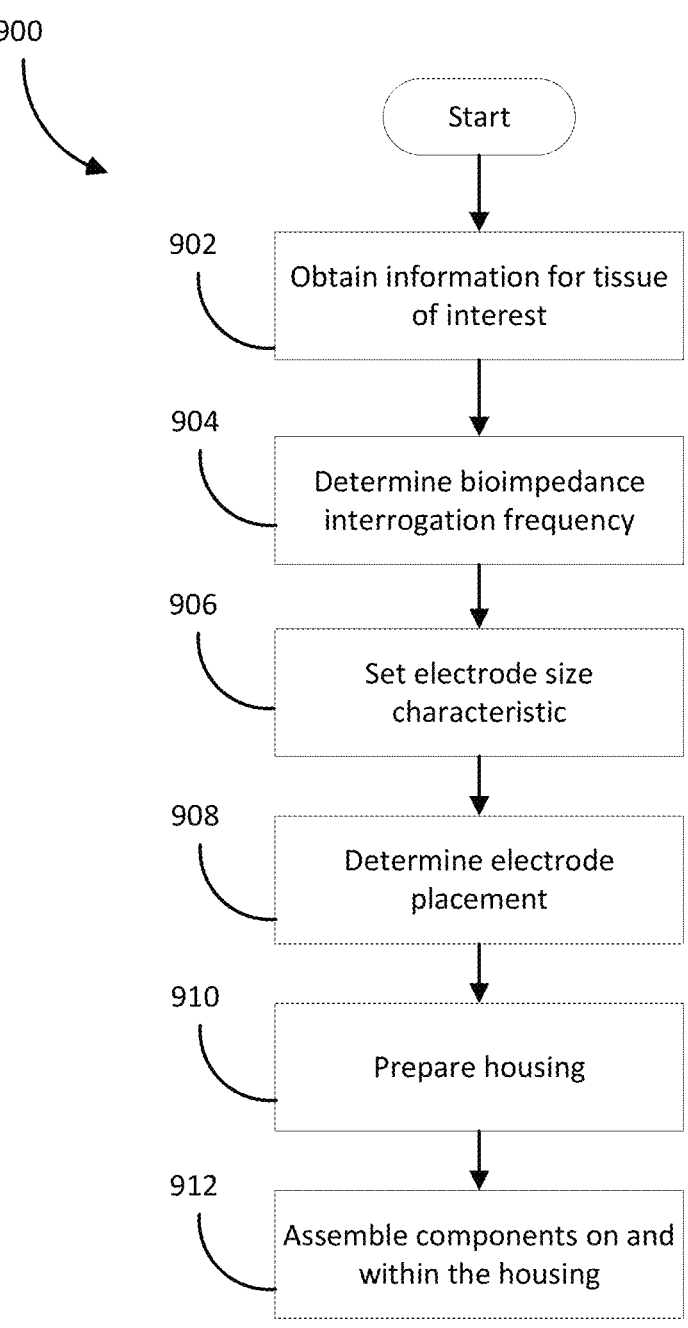
FIG. 9 is a process flow chart illustrating example steps of a method for designing and fabricating a device in accordance with various aspects of the disclosure.

Referring now to FIG. 9, various example methods for manufacturing a device according to aspects of this disclosure will be described with reference to a flowchart 900. At block 902, information relating to a target tissue of interest of a patient is determined. For example, the tissue of interest may be a layer of interest in a patient's GI tract, or may be certain types of inflamed tissue. In other examples, the information may also include a given location within the GI tract at which a bioimpedance measurement is desired. This determination may be made on a device-by-device basis for custom manufacturing of capsules or may be determined for a given manufacturing process (i.e., the "determination" of the tissue of interest is determined for each device by the manufacturing process itself).

At block 904, a bioimpedance interrogation frequency is determined that will be applied by the device(s) to be manufactured. The interrogation frequency may be a set frequency within the ranges described above that is predetermined based upon a likelihood of detecting a category or depth of tissue of interest within the GI tract. For example, a manufacturing process may be configured so that the devices it produces will inject a bio-impedance detecting current at a frequency of 1 kHz, 5 kHz, 10 kHz or the like. These frequencies are roughly in the mid-range of frequencies that might be useful for bioimpedance measurements in a patient's GI tract and provide a number of benefits compared to higher (e.g., around 200 kHz) or lower (e.g., around 100 Hz) frequencies. For example, the inventors have determined that mid-range frequencies for bioimpedance-measuring current have minimal dependency on contact pressure (and, thus, would not require a capsule with a very large diameter and/or very large electrodes); are less susceptible to stray capacitances (and, therefore, have less noise and a more accurate signal); and result in detected impedances reflecting contribution of both extracellular and intracellular spaces, which can offer a wider range of possible types of detections). Thus, for many use cases (e.g., for many types of tissues or tissue conditions, and for many depths of tissues desired to be measured), the inventors have found that mid-range frequencies are particularly useful for collecting physiological information by ingestible capsules for most types of tissues of interest.

Alternatively, a given manufacturing process may be configured to determine a lower frequency current that will be emitted by the devices it produces, such as 100 Hz, 150 Hz, 200 Hz, 250 Hz, or the like. Lower frequency bioimpedance-detecting currents have advantages and disadvantages, and are useful depending on the nature of the tissue of interest to be detected. For example, lower frequency currents are useful for probing extracellular space, and reduce the contribution of intracellular spaces in the impedance signal. They also tend to exhibit a high impedance contribution or capacitance from cellular membranes. Thus, if a device is to be manufactured to test for a given GI condition that benefits from probing of extracellular space or cellular membranes, then a lower frequency will be more helpful. Additionally, lower frequencies require the least amount of power consumption, thus allowing for less expensive batteries and/or smaller batteries to be used in capsules.

In other embodiments, a manufacturing process may produce devices that interrogate bioimpedance at higher frequencies, such as 50 kHz, 100 kHz, 150 kHz, 200 kHz, 250 kHz or the like. These frequencies tend to be best for probing intracellular space, rather than extracellular space. Notably, these interrogation frequencies decrease variation in measured reactance since the contribution from cell membranes is often small or negligible. However, these frequencies tend to be susceptible to measurement of stray capacitances, have low impedance, and high power consumption.

In some embodiments, a manufacturing process may determine a variable frequency for the devices it produces. For example, an onboard microcontroller may be programmed to sweep frequencies within a given range on a periodic basis, such as sweeping a range of mid-level frequencies, such as 500 Hz to 20 kHz, 1 kHz to 10 kHz, or the like. Similarly, the microcontroller could be programmed to sweep similar ranges of high or low frequencies, or to sweep from low frequencies to high frequencies. In some embodiments, a real time signal emitted by the device may be detected by a user via a wireless connection, and the user may be able to control the interrogation frequency remotely.

At block 906, an electrode size characteristic is assigned for a set of electrodes to be fabricated by the manufacturing process. The size characteristics may include diameter, width, length, or thickness of the electrodes. The size characteristic will depend upon the tissue of interest to be interrogated as well as the desired interrogation frequencies. In some embodiments, the diameter of flat, circular, and/or disk-shaped electrodes may be a useful size characteristic to determine in order to coordinate electrical characteristics (as between the tissue of interest and interrogation frequencies), though other characteristics are also contemplated. Diameters may vary from as low as 0.001 mm to 10 mm. However, for most use cases involving ingestible capsules for detecting bioimpedance in the GI tract, the inventors have found that diameters ranging from 0.5 mm to 2 mm are useful.

In some embodiments, smaller electrodes may be utilized for injecting and measuring signals for bioimpedance detection. Smaller electrodes such as 0.2 mm, 0.3 mm, 0.4 mm, 0.5 mm, 0.6 mm, 0.7 mm, 0.8 mm, 0.9 mm, etc. tend to have a higher dependency on capsule size and orientation. Thus, smaller electrodes are more useful for certain types of tissues of interest. For example, if a much more localized measurement with higher specificity is desired (e.g., where lesions or inflammation may be localized or spotty), having smaller electrodes will produce a more precise signal that can be more sensitive to smaller detection areas. Smaller electrodes will also be useful when it is desired to maximize the impedance contribution of mucosal layers of the GI-tract. However, they exhibit variability in their signal from sensor interface impedance, namely electrode-tissue contact resistance. Thus, devices with smaller electrodes may benefit from a higher diameter capsule housing and may be more useful for only certain ranges of frequencies.

Larger electrode embodiments will have less dependency on capsule orientation and will be more likely to detect tissue conditions of interest, although in a less specific way. Larger electrodes, such as e.g., 1.25 mm, 1.5 mm, 1.75 mm, 2 mm, 2.25 mm, 2.5 mm, etc., will exhibit less variability from contact impedance, and will equalize relative contribution of intestinal tissue layers. Thus, for tissue conditions that are more wide-spread in the GI-tract, or where a higher likelihood of detection is desired, larger electrodes can be more beneficial. Similarly, for certain frequency ranges, less dependence on electrode-tissue contact impedance is observed, which can be beneficial for ascertaining accurate physiological information.

At block 908, an electrode placement may be determined, based upon the selected electrode size characteristic and the tissue of interest. The inventors have determined that the relative placement of electrodes with respect to one another, their separation, and the geometry of their placement can be adjusted so as to optimize spatial impedance contribution of the type of tissue a user may desire to interrogate for bioimpedance. In embodiments such as described above, and as demonstrated via the data set forth in FIGS. 6 and 7, width between pairs of injecting and sensing electrodes can be modified to increase or decrease the depth of impedance sensing, which in turn can be utilized to selectively detect which depth of tissue contributes to the bioimpedance sensing. A relatively compact sensor electrode spacing, such as 500 μm, 750 μm, 1 mm, 1.5 mm, etc., is useful to minimize impedance contribution from surrounding tissues—in other words a more localized sensing can be conducted. Additionally, more compact spacing can also achieve higher epithelial impedance contribution.

A much wider sensor width, such as, e.g., 5 mm, 7.5 mm, 10 mm, 12.5 mm, 15 mm, 17.5 mm, or 20 mm, etc., allows a capsule to probe much deeper tissues. In other words, a wider spacing is more beneficial when the target tissue exists at a greater depth from the GI tract interior surface. This, in turn, can also decrease the relative epithelial tissue contribution. Additionally, a wider spacing allows the bioimpedance sensor to be sensitive to more tissue along the length of the capsule, useful for situations in which detection specificity is not as important as having more complete data.

In alternative embodiments, the electrodes need not be aligned in a linear fashion (as described in the exemplary embodiments above, with the electrode placement determination relating to spacing width. Instead, it is contemplated that electrode pairs may be offset relative to one another, and/or the pairs could be in an offset alignment pair-to-pair. Additionally, the electrodes need not be aligned along one side of a capsule (i.e., parallel to a z axis of the capsule), and other geometries of electrodes may be utilized as well such as aligning the electrodes alone a transverse axis, a coronal axis, or on an angle bisecting the transverse and coronal axes of the capsule. Additionally, in some embodiments, more than one bioimpedance sensor may be utilized, such as placing bioimpedance sensors on opposing sides of a capsule, with the sensors being configured to detect bioimpedance at the same, similar, or different depths within the GI tract.

It is contemplated herein that a manufacturing process may involve generating custom sized/shaped electrode patterns on flexible substrates and/or may involve selection of one or more of several pre-printed electrode patterns that may be available. In the latter case, a clinic or other customer may request bioimpedance measuring devices (such as capsules) that are customized to measurement a given intestinal tissue layer for various physiological conditions. Thus, a manufacturing process may select an appropriate flexible electrode to be included in the devices resulting from the process.

At block 910, a housing is prepared (e.g., selected or fabricated) to contain internal electronics as well as to support the bioimpedance electrodes on its exterior surface. As described above, a housing may be a capsule shape, but other shapes are also contemplated, such as elongated box shapes (e.g., with or without curved edges), spheres, etc. The manufacturing process may determine a design and/or dimension of the housing so as to cause greater or lesser contact with an interior of a patient's GI tract. As described above, in circumstances in which smaller electrodes are used (or other circumstances in which contact and contact pressure with the interior tissue of the GI tract is important), a larger diameter or profile of the house may be more desirable. In other circumstances, a smaller diameter or profile may be possible for patient comfort. Thus, in choosing the size of the housing, the manufacturing process takes into account (whether by user input, or automatically) the electrode size, electrode spacing/geometry, and the interrogation frequency. In addition, the housing will define an interior space that surrounds, stores, and protects the electronics of the device, such as a processor, memory, transmitter or transceiver, power source, AC signal generator, etc. Additionally, the housing defines an opening through which the flexible electrode can be in electrical communication with the processor.

At block 912, the components of the device are assembled within or on the housing, and the housing is sealed. The processing circuitry and wireless communication module (which may be the same or separate components, but comprise a processor and transmitter or transceiver) and power source are placed within the housing to protect them from direct contact with fluids/tissues of the body. Leads of the bioimpedance sensor are connected so as to have electrical communication with the processor (located inside the housing), while the electrodes of the sensor remain outside of the housing. The housing is then closed, the electrodes are fixed on the outer surface of the housing, and the housing is then sealed.

It is contemplated that the foregoing manufacturing process may automatically determine a desirable interrogation frequency (or range of frequencies), an electrode size, an electrode geometry/spacing, and a housing size/profile upon receiving a description of the type of tissue condition and/or tissue depth within a GI tract that is desired to be probed in bioimpedance sensing.

When deployed, a customized device such as resulting from process 900 may be used for a variety of purposes. For example, a capsule may be designed as part of a precision medicine procedure, to be tailored to a specific individual and tissue of interest. The capsule may then be ingested by the patient or otherwise introduced in the patient's body, and can begin transmitting bioimpedance data. Depending on the location and extent of a tissue state/condition that is detected, a clinician may be better able to target drug delivery.

What is claimed is:

1. A device comprising:
   a capsule configured to be ingested by a patient and traverse a patient's gastro-intestinal tract, the capsule comprising:
      a processing circuit;

US 12,697,043 B2

17 a power source connected to provide power to the processing circuit;

a bioimpedance sensor comprising four disk-shaped electrodes arranged on a flexible substrate that is contoured around a curved side outer surface of the capsule, the bioimpedance sensor being in electrical communication with the processing circuit through a single opening formed in the curved side outer surface of the capsule to provide a bioimpedance signal to the processing circuit measured by the four disk-shaped electrodes; and a transmitter connected to wirelessly communicate data from the processing circuit outside a patient's body while the capsule is traversing the patient's gastro-intestinal tract.

2. The device of claim 1, wherein the single opening is dimensioned to connect the bioimpedance sensor to an interior port oriented radially.

3. The device of claim 2, wherein the four disk-shaped electrodes include a pair of outer electrodes configured to inject current and a pair of inner electrodes configured to sense voltage.

4. The device of claim 3, wherein each of the four electrodes has a diameter ranging from about 0.5 mm to about 2 mm.

5. The device of claim 3, wherein a spacing between inner electrodes of the pair of inner electrodes is between 0.001 mm and 10 mm.

6. The device of claim 1, wherein the four disk-shaped electrodes are aligned, on said flexible substrate, parallel to a z-axis of the device that extends along a length of the capsule.

7. The device of claim 1, wherein the bioimpedance sensor is configured to measure, with the use of electrical excitation signals at an interrogation frequency ranging from about 1 kHz to about 10 kHz generated inside the capsule, a bioimpedance derived from both extracellular and intracellular spaces of a tissue in contact with said four disk-shaped electrodes.

8. The device of claim 1, wherein the processing circuit includes a potentiostat integrated analog-front end circuit and a Bluetooth® Low Energy microcontroller, wherein the Bluetooth® Low Energy microcontroller is configured to interface the bioimpedance sensor with an external receiving device, and wherein the potentiostat is configured to amplify an output current of the bioimpedance sensor.

* * * * *